United States Patent [19]
Brunel

[11] Patent Number: 5,855,839
[45] Date of Patent: Jan. 5, 1999

[54] PROCESS FOR MANUFACTURING AN INJECTION DEVICE OF THE PRE-FILLED TYPE CONTAINING A DOSE OF LIQUID FOR INJECTION AND INJECTION DEVICE PRODUCED

[75] Inventor: Marc Brunel, Toulouse, France

[73] Assignee: Sanofi (S.A.), Paris, France

[21] Appl. No.: 638,832

[22] Filed: Apr. 29, 1996

[30] Foreign Application Priority Data

May 4, 1995 [FR] France ................................... 95 05462

[51] Int. Cl.⁶ .................................................. B29C 39/02
[52] U.S. Cl. .......................... 264/524; 604/198; 604/110
[58] Field of Search .................................... 264/524, 537; 222/94, 92; 604/110, 111, 192, 194, 195–198

[56] References Cited

U.S. PATENT DOCUMENTS 3,066,670  12/1962  Stauffer .
5,674,203  10/1997  Lewandowski ...................... 604/198 X

FOREIGN PATENT DOCUMENTS

0229204  7/1987  European Pat. Off. .
0325049  7/1989  European Pat. Off. .
0384744  8/1990  European Pat. Off. .
2698546  6/1994  France .
WO 92/17230  10/1992  WIPO .
WO 92/18183  10/1992  WIPO .
WO 93/00942  1/1993  WIPO .
WO 95/04565  2/1995  WIPO .

*Primary Examiner*—Ronald Stright
*Assistant Examiner*—A T Nguyen
*Attorney, Agent, or Firm*—Willaim H. Holt; Willaim R. Hinds

[57] ABSTRACT

The invention relates to a process for manufacturing an injection device of the pre-filled type comprising producing, in a deformable plastics material, a tubular syringe body (101) equipped with an external locking element (104) suitable for deforming radially between retracted and dilated positions, producing a tubular sheath (109) equipped with an internal locking element (110, 111) paired with that of the syringe body (101), fitting the sheath (109) round the syringe body (101), by a relative sliding of these latter permitted by the radial retraction of the locking element (104) of the syringe body (101), and introducing into the syringe body (101) a rigid pre-filled container suitable for bringing the locking element (104) of the said syringe body into its dilated position, enabling an irreversible locking of the sheath (109) to be obtained once it has been brought, after injection, into an advanced, post-use protection position.

8 Claims, 10 Drawing Sheets

PROCESS FOR MANUFACTURING AN INJECTION DEVICE OF THE PRE-FILLED TYPE CONTAINING A DOSE OF LIQUID FOR INJECTION AND INJECTION DEVICE PRODUCED

BACKGROUND OF THE INVENTION

The invention relates to a process for manufacturing an injection device of the pre-filled type containing a dose of liquid for injection. It extends to an injection device produced according to this manufacturing process.

Currently all the pre-filled syringes on the market have a cap, intended to protect the needle prior to use, which is removed for the injection to be administered and then replaced after injection so as to prevent the subsequent risks of pricking with the soiled needle.

A design of this kind has a major disadvantage arising from the fact that when re-capping the needle, the cap must be offered up opposite the end of this needle. This requirement is in fact the cause of relatively frequent accidents due to pricking, with all the risks that such pricks from a soiled needle involve. Furthermore, such syringes offer no safeguard whose purpose is to prevent their re-use and must therefore be the subject of special care as regards their destruction.

Despite these crucial disadvantages, no rational solution, either from the point of view of industrial-scale manufacture or from the point of view of ease of use of the syringes, has as yet been put forward in respect of pre-filled syringes, which aims to equip them with a protection system suitable for avoiding the risks of pricking after use and preventing further use.

The purpose of the invention is to mitigate these disadvantages and its substantial object is to provide an injection device of the pre-filled type with a low cost price and designed to avoid any risk of pricking after use and to prevent any subsequent re-use.

A further object of the invention is to provide a less costly injection device combining the above-mentioned advantages and incorporating a traditional pre-filled syringe of the type currently in use.

A further object of the invention is to provide an injection device permitting the liquid to be injected to be isolated from the injection needle up to the time of the injection.

A further object of the invention is to provide an injection device having a very low "dead" volume and thus enabling very small doses of liquid to be injected.

A further object of the invention is to provide an injection device particularly suitable for permitting an injection requiring the syringes to be held in an inclined position with respect to the point of injection.

To this end the invention provides a process for manufacturing a pre-filled injection device comprising an injection needle, comprising:

producing a tubular syringe body of a deformable plastics material, equipped towards one of its ends, called the rear end, with finger-hold elements and towards its other end, called the front end, with an external locking element suitable for deforming radially between a retracted position and a dilated position, producing a tubular sheath of a shape suitable for being able to slide along the syringe body, comprising an internal locking element paired with that of the said syringe body in the dilated position of this latter, arranged towards one of its ends, called the rear end, offering up the rear end of the sheath opposite the front end of the syringe body and causing the said sheath and syringe body to slide with respect to each other, this sliding being permitted thanks to the radial retraction of the locking element of the said syringe body, so as to bring the rear end of the sheath to rest adjacent to the finger-hold elements of the syringe body in a position, called the injection position, in which the said sheath extends externally along the syringe body and in which at least the front end of the said syringe body is disengaged, introducing into the syringe body a rigid pre-filled container of external cross-section paired with the internal cross-section of the syringe body suitable for bringing the external locking element of the syringe body into its dilated position and preventing any further radial deformation of the said locking element, the said rigid container being equipped with means for injecting the liquid contained in the latter, and locking the tubular body and the rigid container in translation with respect to each other.

The process according to the invention thus comprised producing a syringe body and a sheath:

the assembly of which is obtained, initially, by a simple sliding of the said syringe body and sheath with respect to each other, this sliding being permitted by the radial retraction of the external element of the syringe body, then forming a non-deformable structure thanks to the introduction into the interior of the syringe body of a rigid container designed radially to dilate the external element of the said syringe body and prevent any subsequent radial deformation of the latter, thus guaranteeing an irreversible locking of the sheath in its advanced position.

The manufacture of an injection device according to the invention is thus achieved in two very simple operations each comprising causing an element to slide longitudinally with respect to another. Manufacture of this kind can therefore easily be automated and lead to a high rate of production of injection devices having a low cost price.

Furthermore, the injection device produced is designed to prevent any risk of accident. In fact, it is equipped with a protection sheath caused to slide towards the front, once the injection has been administered, without any risk of pricking because the needle is re-covered by moving this sheath in the direction of the front end of the syringe body. In addition, once it is in its advanced position this sheath is locked in translation with respect to the syringe body, thus preventing any re-use of the injection device.

It should also be noted that the rigid container, which performs the particular function of making the syringe body rigid, can be put in place either in a preliminary phase at the time of manufacture or solely at the time of use of the injection device.

It is appropriate to stress that the international patent application WO-95 04 565 describes a suction syringe comprising a protection sheath, and of which a priori the sheath is caused to slide along the syringe in order to assemble these elements.

Nevertheless, the syringe is produced from a rigid plastics material and also has a rectangular cross-section, and so it cannot be deformed radially, unlike that of the invention.

In practice therefore, the sheath can only slide along the syringe either if this syringe is deformed by nipping by a mechanical or manual action, or the rear lugs 30, 31 of the sheath are spread by a mechanical or manual action.

Furthermore it should be noted that this patent specifies that:

the windows provided in the sheath and the syringe have the sole function of enabling the dose container to be seen, this dose container is not a rigidifying element intended to ensure that the sheath is irreversibly locked in its advanced position, since because of the design of the locking elements, this irreversible locking is obtained whether the dose container is housed in the syringe body or not.

In fact, even if this patent describes an injection device whose manufacturing process has certain similarities with that of the invention, the general concept on which the invention is based differs totally from that of the process of this patent.

According to a first preferred embodiment, a syringe body is produced comprising a peripheral wall equipped with at least one longitudinal slot opposite the external locking element, suitable for permitting the radial deformations of the said locking element.

In this case the radial deformations of the external element of the syringe body are permitted thanks to the presence of at least one slot, which leads this external element to retract so as to enable the internal locking element of the sheath to pass and then to dilate when the rigid container is introduced.

According to a second preferred embodiment, a syringe body is produced comprising a front end portion in the shape of a truncated cone of decreasing cross-section in the direction of the front end of the said syringe body, and on which the external locking element is arranged, the said truncated-cone-shaped portion being equipped longitudinally with weakness zones suitable for permitting its radial dilation.

In this case the front end of the syringe body is preformed, when the said syringe body is moulded, so as to form the external locking element in a retracted position permitting the internal locking element of the sheath to pass, the presence of weakness zones enabling this external locking element to be brought into its dilated position radially when the rigid container is introduced.

According to a preferred embodiment intended to prevent any untimely sliding of the sheath before and during the injection, the respective rear ends of the sheath and of the syringe body are secured, in their injection position, by holding means suitable for being able to yield under the effect of a longitudinal tensile force applied to the sheath and intended to make it slide towards the front with respect to the syringe body.

Such holding means may comprise either paired enclosing structures provided at the respective rear ends of the sheath and of the syringe body, enabling them to be secured in a detachable manner. They may also comprise at least one securing point achieved by any per se known method such as heat welding, ultrasonic welding etc.

According to a first preferred embodiment:

a syringe body is produced which is equipped with a front end having the form of a sleeve, a rigid container comprising a pre-filled syringe with an injection needle and having a front portion of a shape suitable for being accommodated in the sleeve of the syringe body, so that the injection needle extends in the extension of the said syringe body, is introduced into the syringe body.

This embodiment enables an injection device to be produced which comprises, by way of rigid container, a traditional pre-filled syringe like the current glass syringes, whilst equipping the said syringes, at reduced cost, with a protection system which guarantees against any risk of accident after use.

According to a second preferred embodiment:

a syringe body is produced which is equipped towards its front end with a nose pierced longitudinally by a bore of cross-section suitable for accommodating an injection needle, an injection needle is introduced into the bore of the nose of the syringe body, so that it has an active injection portion in the extension of the said syringe body, and a piercing portion opening into the interior thereof, the injection needle is secured in the bore of the nose of the syringe body, and a rigid, pre-filled container equipped with a sealing element suitable for being pierced by the piercing portion of the injection needle is introduced into the syringe body.

This embodiment enables an injection device to be produced which comprises, by way of rigid container, any traditional container whose sealing system can be pierced by a needle in order to administer the injection. A container of this kind can thus comprise a simple cartridge of the type used, for example, in the dental field.

According to a third preferred embodiment:

a syringe body is produced which is equipped with a front end sealed by a front end wall pierced by an aperture, and comprises a longitudinal bore, arranged in its peripheral wall, extending between the said front wall and a radial internal duct opening in the interior of the said syringe body, this radial duct being arranged at a distance from the front wall and being juxtaposed longitudinally to a shoulder delimiting, inside the syringe body, an end chamber, incorporating the said radial duct, of smaller cross-section than the standard internal cross-section of the said syringe body, an injection needle is introduced into the longitudinal bore so that it has an active injection portion in the extension of the front wall of the syringe body, the injection needle is secured in the longitudinal bore of the syringe body, and into the interior of the syringe body is introduced a rigid pre-filled tube of cross-section suitable for coming to rest against the internal shoulder of the said syringe body, the said rigid tube being sealed, towards each of its ends, by a sliding plug, respectively called front and rear, the front plug having a shape suitable for being accommodated in the end chamber of the syringe body, when the rear plug slides, in a position in which it comes to rest against the front wall and disengages the radial duct.

This embodiment enables injection devices to be produced which have a very low "dead" volume, particularly suitable for injecting very small doses of liquid.

Furthermore, because of the position of the injection needle arranged laterally with respect to the syringe body, and by means of a correct orientation of the chamfer of the active injection portion thereof, this injection device is particularly suitable for permitting an injection (in the abdomen for example) which requires the injection needle to be held in an inclined position with respect to the injection point.

Furthermore, for each of the above-mentioned applications, the front end of the syringe body is advantageously capped, in traditional manner, in order to protect the needle prior to use and to prevent any risk of pricking with the latter.

The invention extends to an injection device of the pre-filled type comprising:
- a tubular syringe body made of a deformable plastics material, equipped towards one of its ends, called the rear end, with finger-hold elements and towards its other end, called the front end, with an external locking element suitable for deforming radially between a retracted position and a dilated position,
- a tubular sheath of internal cross-section suitable for being able to slide along the syringe body, equipped with an internal locking element paired with that of the said syringe body in the dilated position of this latter, arranged towards one of its ends, called the rear end, the said sheath being suitable for being able to slide between two positions:
  - a rear, injection, position in which the rear end of the sheath rests adjacent to the finger-hold elements of the syringe body on the one hand, and at least the front end of the syringe body is disengaged on the other hand,
  - a front, post-use protection, position in which the respective locking elements of the sheath and of the syringe body are in a state of cooperation on the one hand, and the sheath covers the front end of the syringe body and extends in the extension thereof on the other hand,
- a rigid pre-filled container introduced into the interior of the syringe body and of external cross-section paired with the internal cross-section of the said syringe body,
- and means for the relative locking in translation of the rigid container and the syringe body.

According to a first preferred embodiment the syringe body comprises a front end portion of decreasing cross-section in the direction of the front end of the said syringe body, on which portion the external locking element is arranged, the said truncated-cone-shaped portion being equipped longitudinally with weakness zones suitable for permitting its radial dilation.

According to a second preferred embodiment the syringe body comprises a peripheral wall equipped with at least one longitudinal slot extending opposite the external locking element, suitable for permitting the radial deformations of the said external locking element.

In this case, furthermore, the syringe body advantageously has a peripheral wall equipped with two diametrically opposed longitudinal slots. This arrangement of longitudinal slots is in fact advantageous when the syringe bodies are produced by plastic moulding.

According to a further feature of the invention:
- the locking element of one of the components, syringe body or sheath, has the form of an annular boss comprising an annular groove and notches, arranged either side thereof,
- the locking element of the other component, sheath or syringe body, comprises an annular rib delimiting a section paired with the section of the bottom of the groove of the boss of the first component.

Furthermore, the notches of the locking element arranged on one of the components, syringe body or sheath, and located towards the end of the said component, advantageously have a thickness greater than that of the second notches delimiting the groove of the said locking element.

As a result, the first notches cause a radial deformation of the syringe body which facilitates the passage of the second notches and ensures an easy fitting of the sheath on the said syringe body.

Furthermore, according to a further feature of the invention, the second notches of the locking element arranged on one of the components, syringe body or sheath, have a front face which extends according to a chord of the said component and is suitable for obtaining at the said notches a perimeter at least equal to that of the other component opposite the latter's annular rib.

The sheath is thus simply deformed triangularly on the passage of the second notches over the annular locking rib, without having to be radially dilated in order for this passage to take place, which facilitates bringing the said sheath into its advanced locking position, after use.

According to another feature of the invention the syringe body has an internal diameter appreciably larger than the external diameter of the rigid container, and comprises longitudinal internal ribs opposite the internal locking element of the said syringe body, determining a diameter paired with the external diameter of the rigid container.

This arrangement enables a label to be placed round the rigid container and an intimate contact between the syringe body and the rigid container to be obtained when the latter is introduced, despite the extra thickness that this label forms.

According to a first preferred embodiment of this injection device:
- the syringe body comprises a front end having the form of a sleeve,
- the pre-filled rigid container comprises a pre-filled syringe having an injection needle, and having a front portion of a shape suitable for being accommodated in the sleeve of the syringe body, so that the injection needle extends in the extension of the said syringe body.

Furthermore, when the pre-filled syringe is traditionally equipped with a rear end comprising a finger-hold flange, the syringe body then preferably comprises, at its rear end, radial notches suitable for accommodating the said flange and for ensuring the locking in translation of the said pre-filled syringe.

Furthermore, the radial notches are preferably arranged in a cup-shaped ring of a diameter greater than that of the syringe body and arranged in the rear extension of the said syringe body, the said ring being suitable for serving as a frontal rest for the rear end of the sheath.

The injection device advantageously also comprises an annular deformable band arranged to be acted on by the flange of the syringe, so as to ensure a play-free locking thereof in the radial notches.

The advantage of such a band is to ensure a perfect locking of the syringe, despite the variations in thickness of the latter's flange due to manufacturing tolerances.

According to a second preferred embodiment of this injection device:
- the syringe body is equipped, towards its front end, with a nose pierced longitudinally by a bore accommodating an injection needle so that the latter has an active injection portion in the extension of the said syringe body, and a piercing portion opening into the interior thereof,
- the rigid, pre-filled container comprises a cartridge equipped with a sealing element suitable for being pierced by the piercing portion of the injection needle.

Furthermore, the sealing element of the cartridge preferably then comprises a plug suitable for being pierced and arranged, in an initial phase, so as to be at a distance from the end of the piercing portion of the injection needle, the said cartridge being sealed towards its other end, by a second plug performing the function of plunger.

An arrangement of this kind enables the liquid to be injected to be isolated from the injection needle up to the time of the injection. As a result and initially, this liquid is not in contact either with the needle or the adhesive used to secure it, and so is not at risk of contamination. Furthermore the needle does not have to be sealed, such as in the traditional manner by inserting it into the bottom of a cap, and its penetration qualities are therefore wholly preserved.

According to a further feature of the invention which provides this second preferred embodiment, the syringe body comprises, at its rear end, an internal rib suitable for ensuring the locking in translation of the cartridge introduced into the said syringe body.

According to a third preferred embodiment of this injection device:

- the syringe body is equipped with a front end sealed by a front end wall pierced by an aperture, and comprises a longitudinal bore arranged in its peripheral wall, housing an injection needle so that the latter has an active injection portion in the extension of the front wall, the said bore extending between the said front wall and a radial internal duct opening in the interior of the said syringe body, this radial duct being arranged at a distance from the front wall and being juxtaposed longitudinally to a shoulder delimiting, inside the syringe body, an end chamber incorporating the said radial duct, of smaller cross-section than the standard internal cross-section of the said syringe body,
- the rigid pre-filled container comprises a cartridge of cross-section suitable for coming to rest against the internal shoulder of the said syringe body, the said cartridge being sealed, towards each of its ends, by a sliding plug, respectively called front and rear, the rear plug performing the function of plunger, and the front plug having a shape suitable for being accommodated in the end chamber of the syringe body, when the rear plug is actuated, in a position in which it comes to rest against the front wall and disengages the access to the radial duct.

An injection device of this kind has a very low "dead" volume and is particularly suitable for injecting small doses of liquid. Furthermore, it enables the liquid to be injected to be isolated from the injection needle up to the time of the injection.

Furthermore, the syringe body then preferably comprises, at its rear end, an internal rib suitable for ensuring the locking in translation of the cartridge introduced into the said syringe body.

Further features, objects and advantages of the invention will emerge from the detailed description below with reference to the accompanying drawings which show five preferred embodiments thereof by way of non-exhaustive examples. These drawings form an integral part of this description and are as follows:

DESCRIPTION OF THE PREFERRED EMBODIMENTS

The injection devices shown by way of examples in the illustrations all comprise three main components consisting of a syringe body suitable for having an ability to deform radially, a sheath suitable for being fitted round the syringe body and intended to protect the needle after injection, and a pre-filled, rigid container introduced into the syringe body, either at the time of manufacture or only prior to injection, and intended in particular to give the syringe body a non-deformable character.

Furthermore the syringe body and the sheath of these devices are made of a deformable plastics material such as butadiene styrene.

Figure 1:
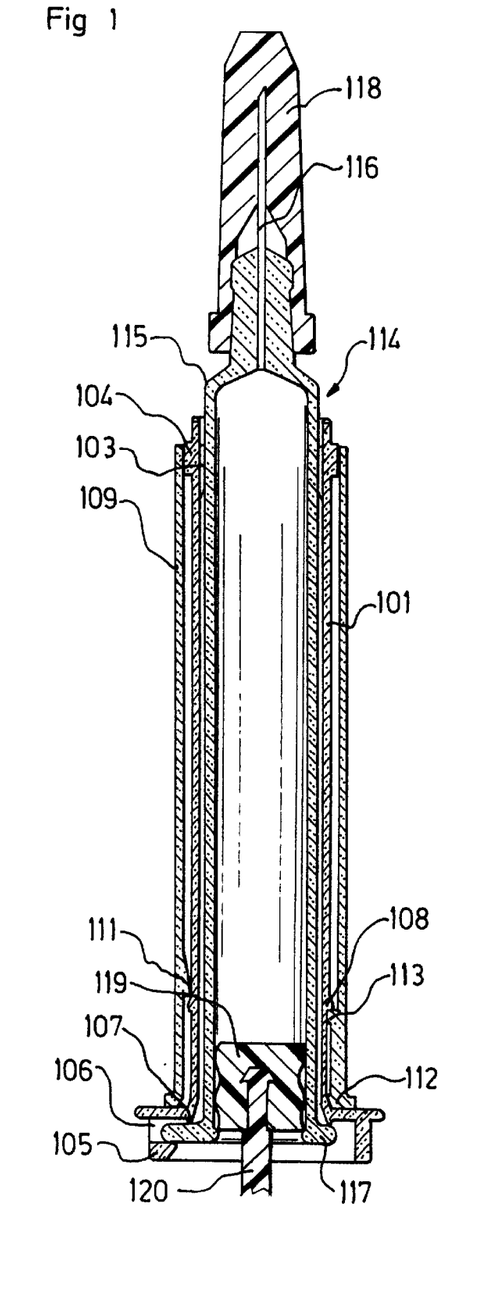
FIG. 1 is a longitudinal section on an axial plane of a first embodiment of an injection device according to the invention, shown prior to use.
Figure 2:
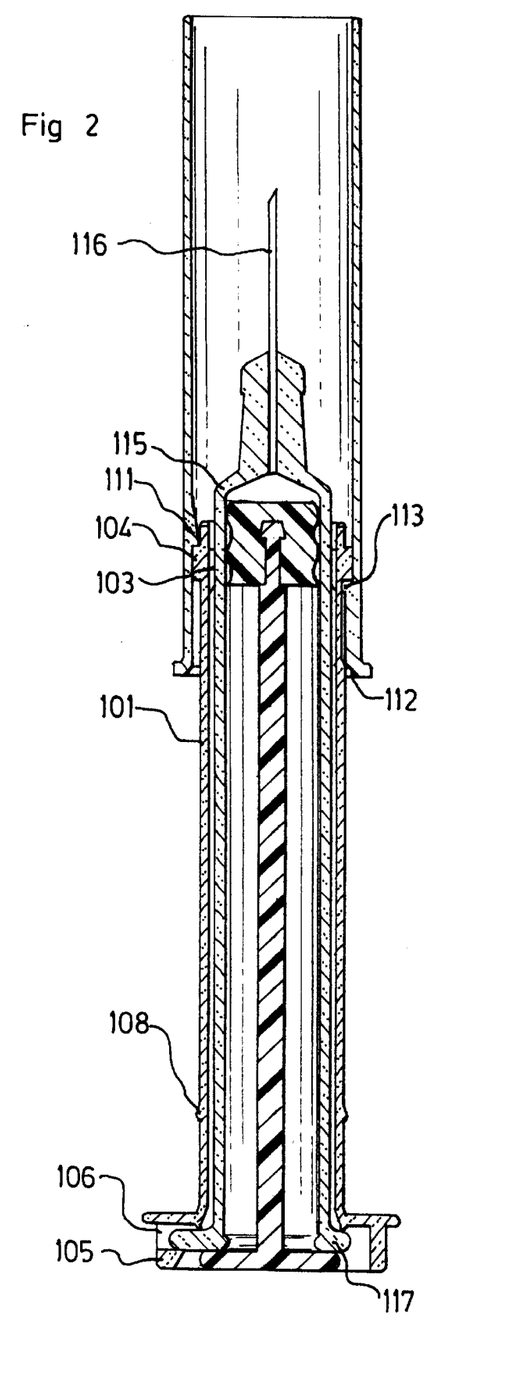
FIG. 2 is a longitudinal section on an axial plane showing this injection device after use.
Figure 3:
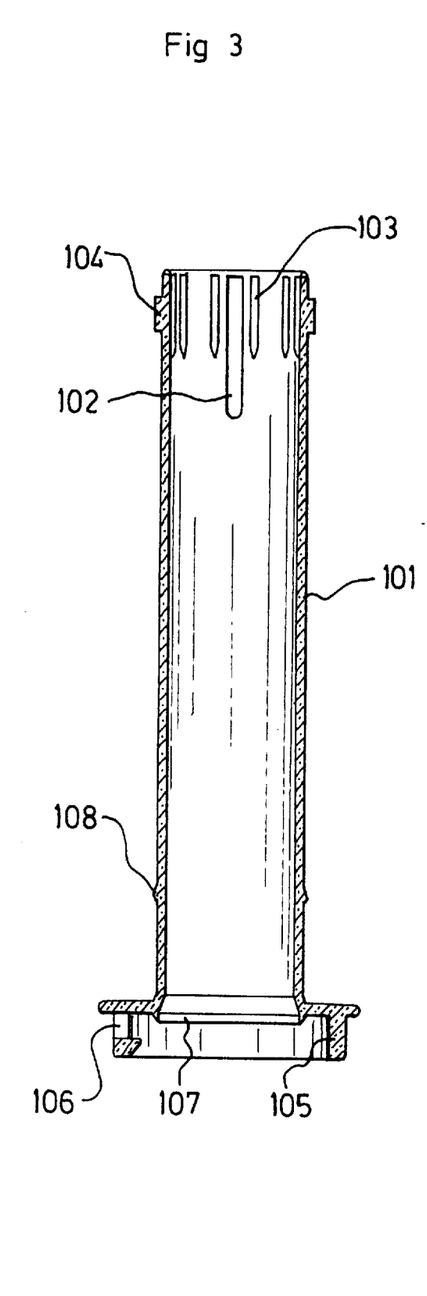
FIG. 3 is a longitudinal section on an axial plane of the syringe body of this injection device.
Figure 4:
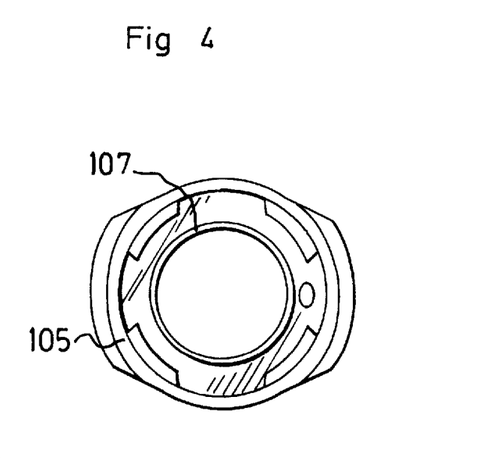
FIG. 4 is a front view of the rear end of this syringe body.
Figure 5:
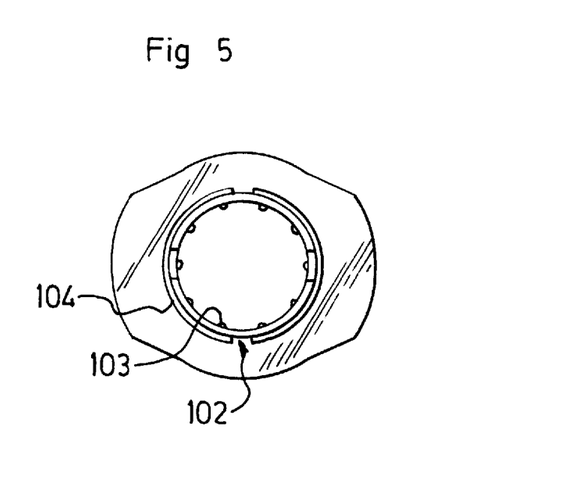
FIG. 5 is a front view of the front end of this syringe body.

Firstly, the injection device shown in FIGS. 1 to 7 comprises a tubular syringe body 101 shown in FIGS. 3 to 5, the peripheral wall of which is equipped with two diametrically opposed longitudinal slots such as 102.

Each of these slots 102 is provided at the front portion of the syringe body 101, has a length at least equal to the locking element, described below, of the said syringe body 101, and extends at least opposite the said locking element. Furthermore they do not emerge at the front end of the syringe body 101 so as to prevent the said syringe bodies from entangling in each other when being transported on an automated production line.

This syringe body 101 also comprises internal longitudinal ribs such as 103 extending at its front end portion and uniformly distributed round the axis of symmetry of the said syringe body.

In addition, in its front end portion this syringe body 101 comprises an external locking element comprising an external annular rib 104.

On the rear end side, this syringe body 101 is extended by a cup-shaped ring 105 of diameter greater than that of the said syringe body which forms the finger-hold element of the said syringe body, and in which radial notches such as 106 are provided.

Furthermore, a deformable annular band 107 is arranged inside this ring 105 directly in the extension of the syringe body 101.

Finally this syringe body 101 comprises an external annular rib 108 provided at a pre-determined distance from its rear end as explained below.

Figure 6:
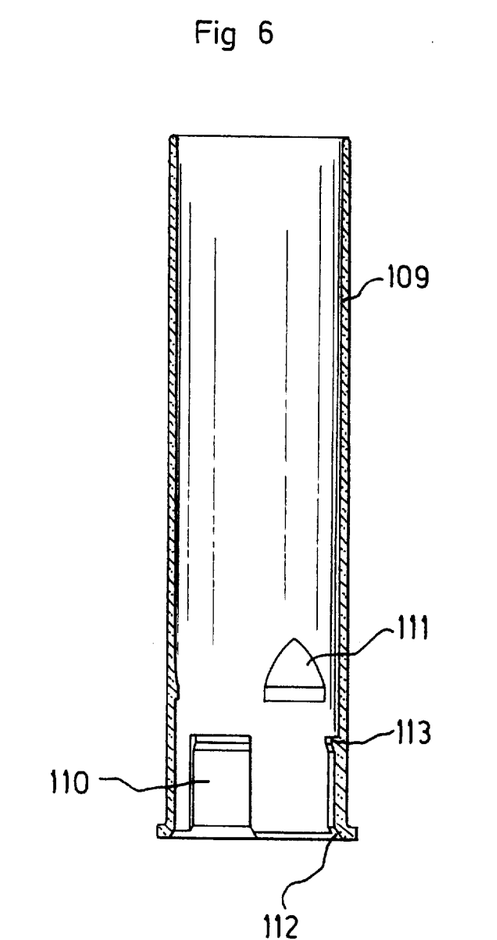
FIG. 6 is a longitudinal section on an axial plane of the sheath of this injection device.
Figure 7:
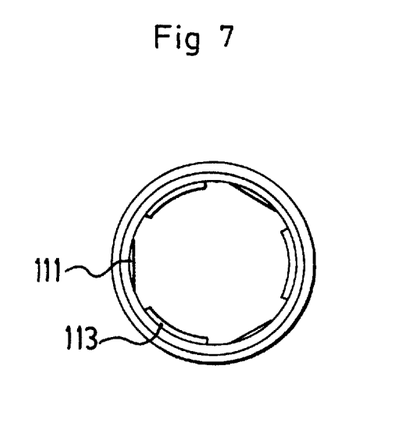
FIG. 7 is a front view of the rear end of this sheath.
Figure 8:
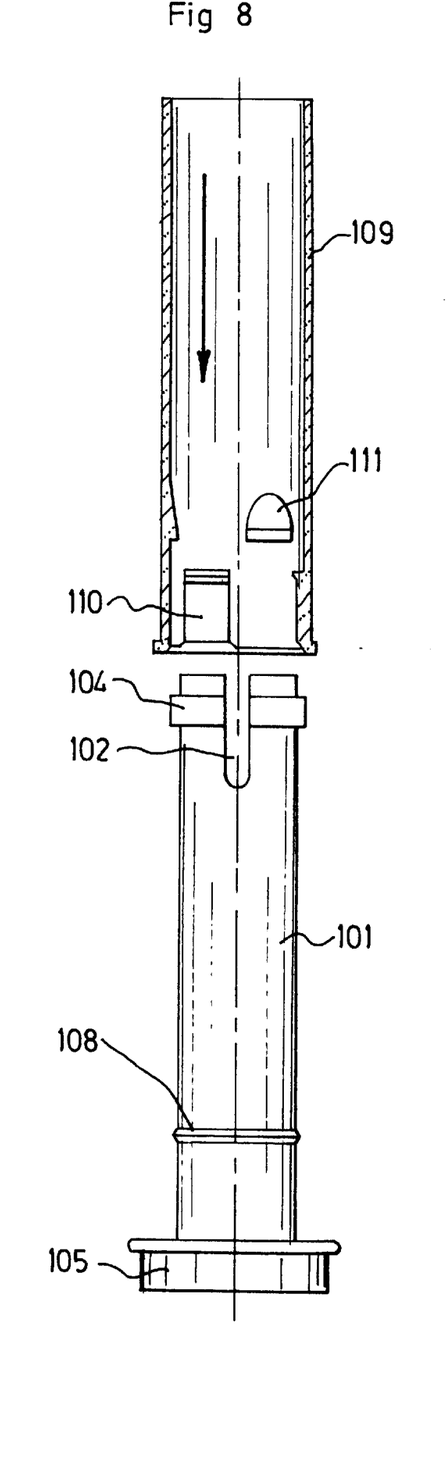
FIGS. 8 to 11 show the various stages of manufacture of this injection device.

As shown in FIGS. 6 and 7, the sheath 109 of this injection device comprises a cylindrical sheath of internal diameter paired with the external diameter of the annular locking rib 104 of the syringe body 101.

This sheath 109 comprises internal locking means arranged at its rear end and intended to cooperate with the external rib 104 of the syringe body 101.

These locking means comprise two sets of notches such as 110, 111, offset axially so as to delimit, between the said sets of notches, an annular chamber suitable for accommodating the external rib 104 of the syringe body 101.

Furthermore the notches 110, 111 of each set are uniformly distributed round the longitudinal axis of the sheath 109, and the notches of each set are offset with respect to those of the other set so as to enable the sheath 109 to be withdrawn.

Firstly the rear notches 110 extend from the rear end of the sheath 109 and have the form of annular sectors projecting with respect to the internal surface of the said sheath.

Furthermore these rear notches 110 have a chamfered rear end 112 and comprise an annular rib 113 forming an extra thickness at their front end.

As shown in FIG. 7, the notches 111 of the other set are provided so that their front surface extends according to a chord of the internal surface of the sheath. Furthermore, they have a decreasing thickness in the direction of the front end of the sheath 109, which gives them the shape of an ogive when viewed from the front and as shown in FIG. 6.

In addition, these notches 111 have a maximum thickness less than the thickness of the rear notches 110 opposite the front annular rib 113 of these latter.

For its part, the syringe of this first embodiment is a pre-filled syringe 114 of traditional type, such as made of glass for example, and traditionally comprising:

a front nose 115 on which an injection needle 116 is fitted,
an external flange 117 at its rear end, suitable for being accommodated in the radial notches 106 of the syringe body 101, so as to ensure a locking in translation of the said syringe,
a cap 118 to protect the injection needle 116 prior to use, in the bottom of which the end of the said needle is inserted to prevent any leakage of liquid,
and a plug 119 performing the function of plunger and associated with a plunger rod 120.

The assembly stages of an injection device of this kind are shown in FIGS. 8 to 11.

Firstly the sheath 109 is offered up opposite the front end of the syringe body 101 (FIG. 8) and then fitted onto it.

Figure 9:
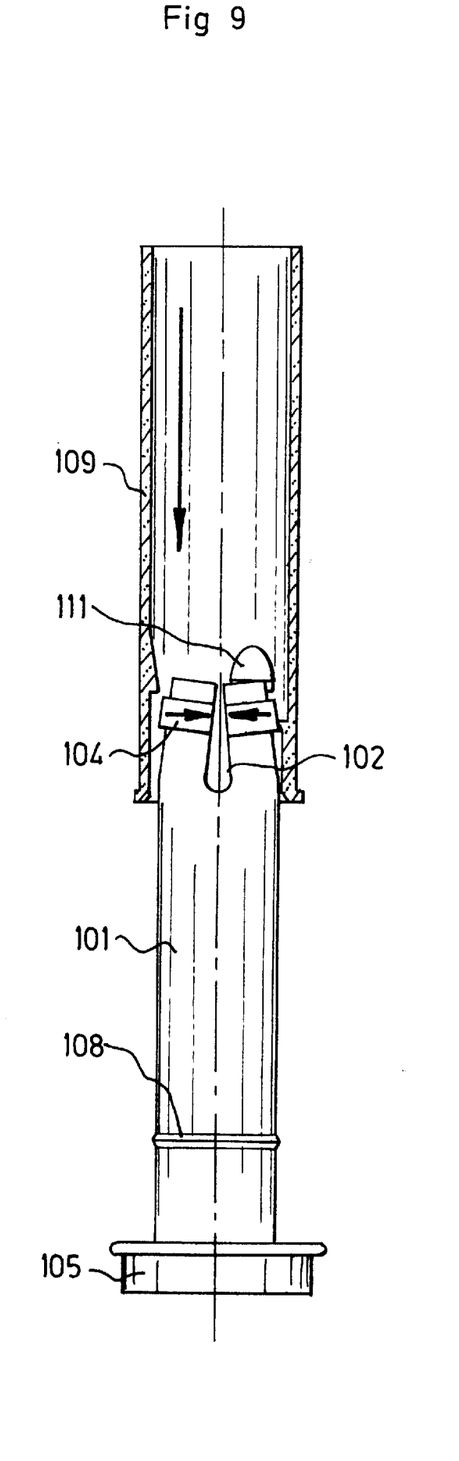

In the course of this fitting the rear notches 110 of the sheath 109 cause a radial retraction of the annular rib 104 of the syringe body 101, because of the presence of the slots 102 (FIG. 9).

Furthermore, because these rear notches 110 have a thickness greater than that of the other notches 111, this radial deformation is such that the passage of these notches 111 over the annular rib 104 presents no problem.

After use this passage of the notches 111 over the annular rib 104 is also facilitated by the shape of these notches 111 which lead to a simple triangular deformation of the sheath 109 being obtained without increasing the diameter of the latter in the course of this passage.

Figure 10:
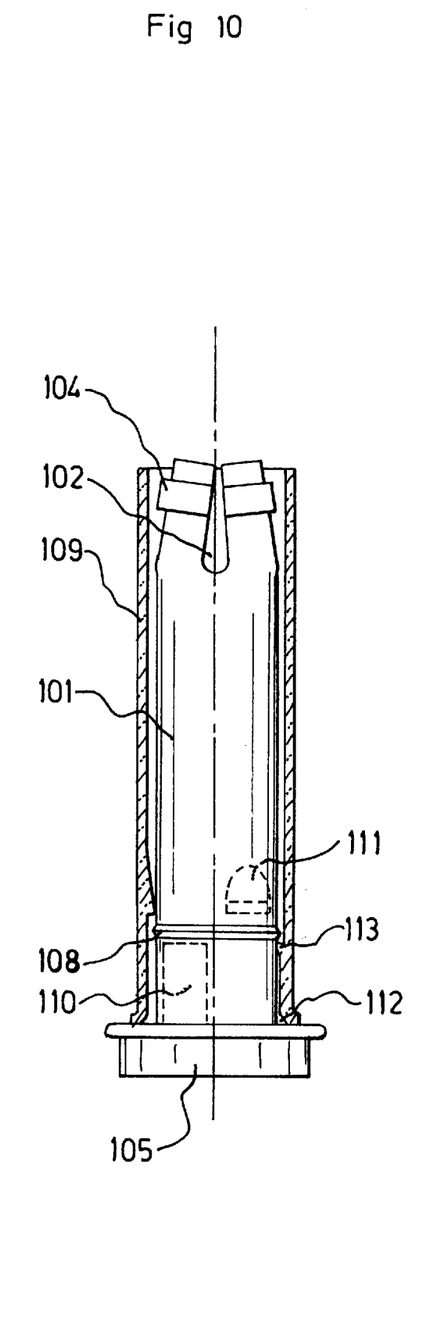

When fitting is completed, and as shown in FIG. 10, the syringe body 101 is totally housed inside the sheath 109, the rear end of which rests frontally against the ring 105 of the said syringe body.

Furthermore, in this position the rear notches 110 of the sheath 109 cooperate with the annular rib 108 of the syringe body 101, leading to a relative locking in translation of the said components, unless a sufficient tensile force is applied to cause the rear notches 110 to cross the rib 108.

Furthermore, as deliberately emphasized in FIG. 10, the locking element 104 of the syringe body 101 retains a residual radial deformation resulting from the nature of the material from which this syringe body 101 is made.

Figure 11:
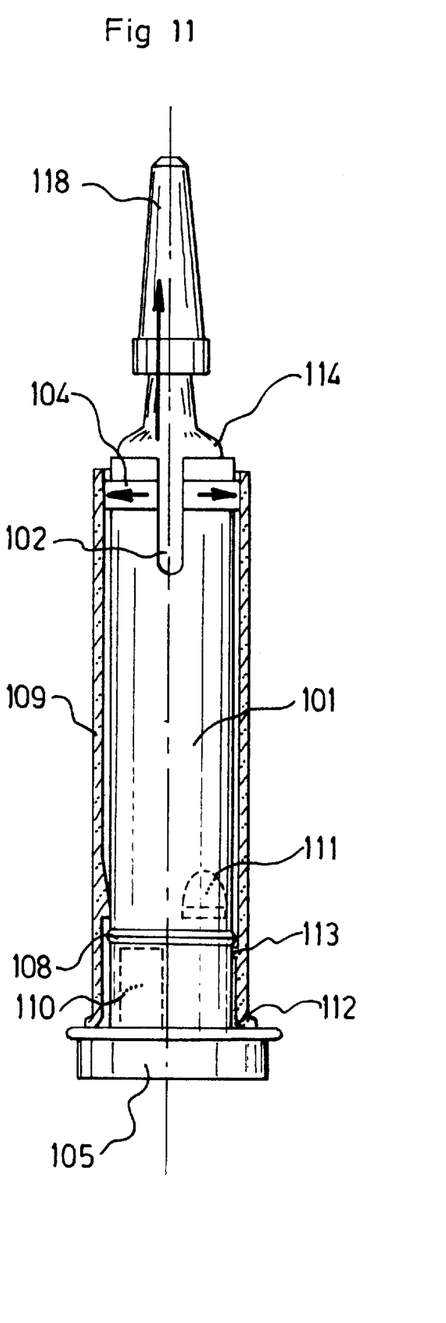

The last stage comprises introducing the pre-filled syringe 114 into the interior of the syringe body 101. At the time of this introduction, because of the presence of the internal ribs 103, the pre-filled syringe 114 tends radially to dilate the annular rib 104 of the syringe body 101.

When introduction is completed the flange 117 of the syringe 114 is housed in the radial notches 106 in which it is locked in a play-free manner because of the presence of the band 107.

The syringe body 101 and the sheath 109 then form a non-deformable structure thus guaranteeing a locking of the sheath 109 when it is brought into its advanced position, after use of the injection device.

Furthermore, it should be noted that when the sheath 109 is caused to slide forwards, the fact that the rear notches 110 have a front rib 113 enables the said notches to be prevented from rubbing against the rib 108 of the syringe body 101 and opposing this translation.

FIGS. 12a, 12b, 13a, 13b show a second embodiment of an injection device according to the invention which comprises a sheath 109 and a pre-filled syringe 114 similar to those described above, and a syringe body 121, the rear part of which is also identical to that of the syringe body 101 described above, and is not therefore shown.

Figure 12A:
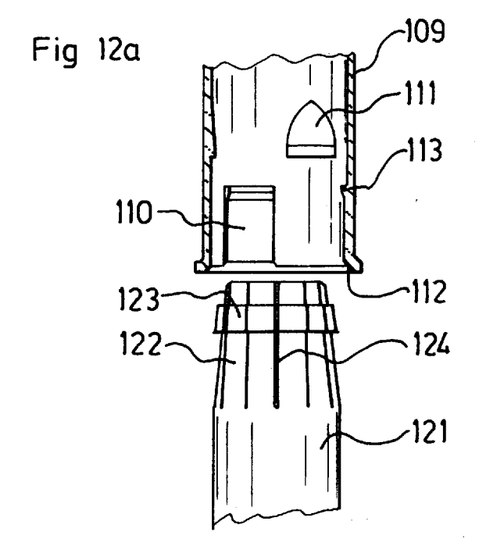
FIG. 12a shows a second embodiment of the injection device according to the invention prior to the assembly of the sheath and the syringe body, in which the sheath is shown in longitudinal section on an axial plane and the syringe body in a longitudinal view.
Figure 12B:
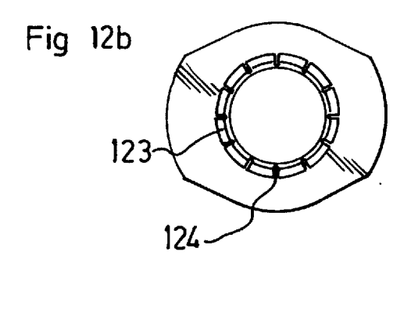
FIG. 12b is a front view of the front end of the syringe body of this injection device in the radially retracted state of this latter.

The special feature of this syringe body 121 lies in the fact that it comprises a front portion 122 on which an external annular locking rib 123 is provided and which is preformed so as to have a truncated cone shape of decreasing cross-section in the direction of the front end of the said syringe body.

This truncated-cone-shaped portion 122 also has weakness zones 124 comprising longitudinal lines of less thickness distributed round the axis of the syringe body 121.

As shown in FIG. 12a, a design of this kind enables the sheath 109 to be fitted easily, because the annular rib 123 of the syringe body 121 is in a radially retracted position permitting the passage of the notches 110 and 111.

Figure 13A:
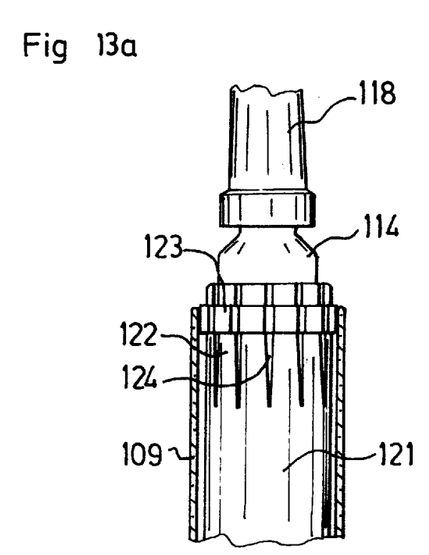
FIGS. 13a and 13b are views of this injection device corresponding to FIGS. 12a and 12b, after assembly of the syringe body and the sheath and introduction of the rigid container.
Figure 13B:
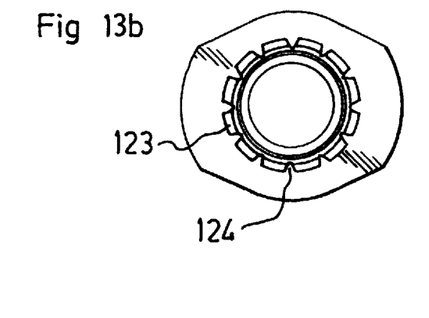

Furthermore, as shown in FIG. 13a, the subsequent introduction of the syringe 114 into the interior of the syringe body 121, once the sheath 109 is in place, leads to the truncated-cone-shaped portion 122 and hence the annular rib 123 being dilated radially as a result of the presence of the weakness zones 124.

Because of this, an injection device with the same advantages as the one described above is also obtained.

Figure 14:
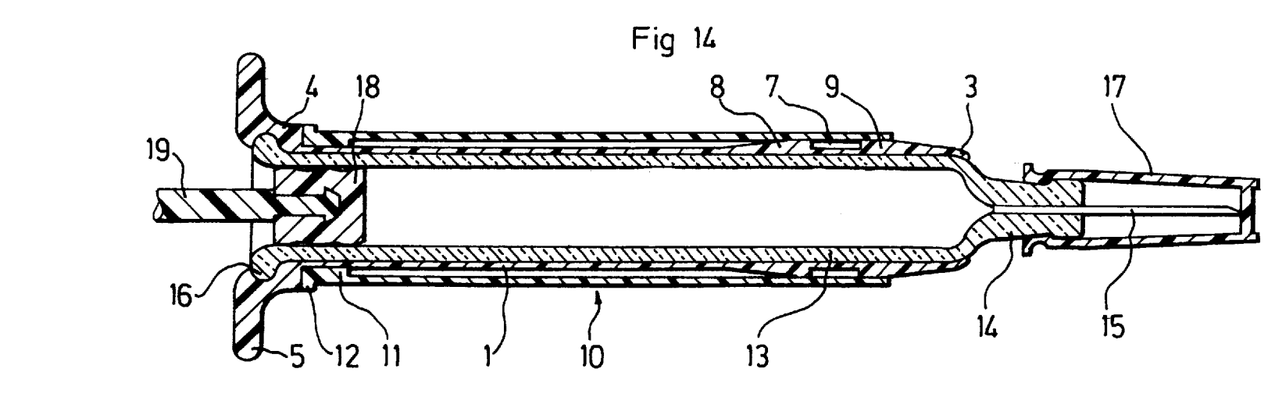
FIG. 14 is a longitudinal section on an axial plane of a third embodiment of an injection device according to the invention, shown prior to use.
Figure 15:
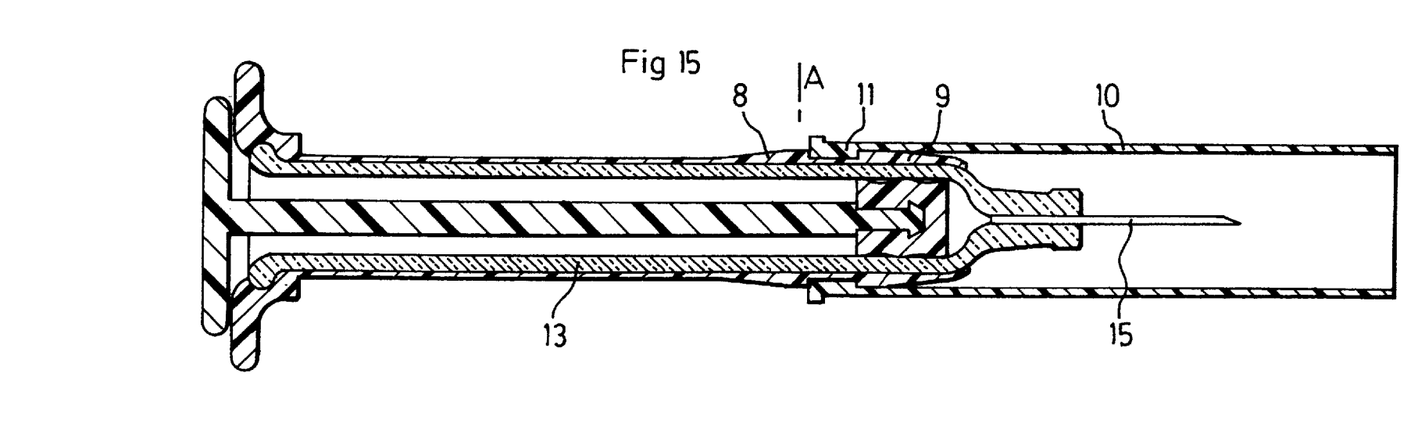
FIG. 15 is a longitudinal section on an axial plane showing this injection device after use.
Figure 16:
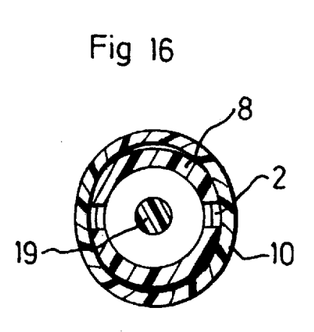
FIG. 16 is a transverse section on a plane A of this injection device, showing the sheath when it has finished sliding.

The embodiment of an injection device according to the invention which is shown in FIGS. 14 to 16 is similar in its principle to that of the first embodiment. It therefore comprises a tubular syringe body 1, shown in FIG. 17, the peripheral wall of which is equipped with two diametrically opposed longitudinal slots such as 2.

Figure 17:
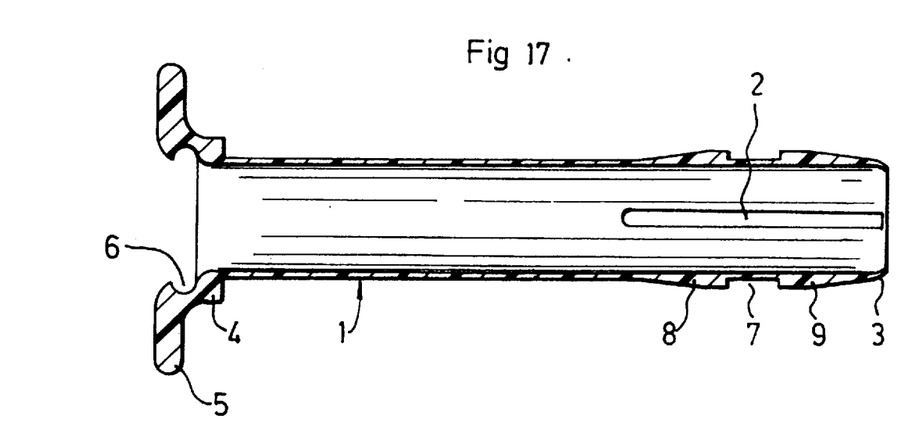
FIG. 17 is a longitudinal section on an axial plane of the syringe body of this injection device.

Towards its front end, this syringe body 1 forms a sleeve 3 of decreasing cross-section suitable for forming a retaining seat for the pre-filled syringe.

Towards its rear end this syringe body 1 has an external annular shoulder 4 forming a frontal rest surface, and two finger-hold lugs, such as 5, extending symmetrically either side of the rear portion of this shoulder. Opposite the lugs 5 this shoulder 4 also comprises an internal notch 6 of rounded cross-section, for locking the syringe as described below.

Finally, in its front end portion this syringe body 1 comprises an external locking element having the form of an annular boss interrupted at right angles to each slot 2, comprising an annular groove 7 and two inclined ramps 8, 9 for access to the said groove, extending longitudinally either side thereof.

The sheath of this third embodiment comprises a cylindrical sheath 10 of internal diameter paired with the external cross-section of the boss 7–9 of the syringe body.

Towards its rear end this sheath 10 comprises an internal annular rib 11 delimiting an internal section paired with the standard external section of the syringe body.

Finally, at its rear end, this sheath 10 comprises an external shoulder 12 forming, with the rear end face of the rib 11, a frontal rest surface paired with that of the shoulder 4 of the syringe body 1.

For its part, the syringe of this first embodiment is a pre-filled syringe 13 of traditional type, comprising as before:

- a front nose 14 on which an injection needle 15 is fitted, and forming a neck, the base of which is suitable for cooperating with the internal surface of the sleeve 3 of the syringe body,
- an external flange 16 at its rear end, suitable for being accommodated in the notch 6 of the syringe body 1, so as to ensure a locking in translation of the said syringe,
- a cap 17 to protect the injection needle 15,
- and a plug 18 performing the function of plunger and associated with a plunger rod 19.

As described above, the assembly of such an injection device comprises causing the sheath 10 to slide longitudinally along the syringe body until the respective rear shoulders 4, 12 of these latter come to rest in a frontal manner.

When this assembly is completed the rear ends of the sheath 10 and of the syringe body 1 are secured, opposite the junction faces of the shoulders 4, 12, by means of at least one securing point, produced by heat welding, ultrasonic welding etc., which is suitable for being able to yield under the effect of a longitudinal tensile force applied to the said sheath and intending to make it slide forwards.

Finally, the pre-filled syringe is introduced into the syringe body 1 in which it becomes locked because of the cooperation of the flange 16 and the notch 6, ensuring, once introduced, the rigidification of the said syringe body and forming a non-deformable structure with the latter.

When this assembly is completed the injection is administered in traditional manner after the protective cap 17 has been removed.

After injection, a tensile force applied to the sheath 10 enables it to be slid forwards to bring the rib 11 of the said sheath inside the groove 7 of the syringe body, a position in which the injection needle 15 is protected by the sheath.

Figure 18:
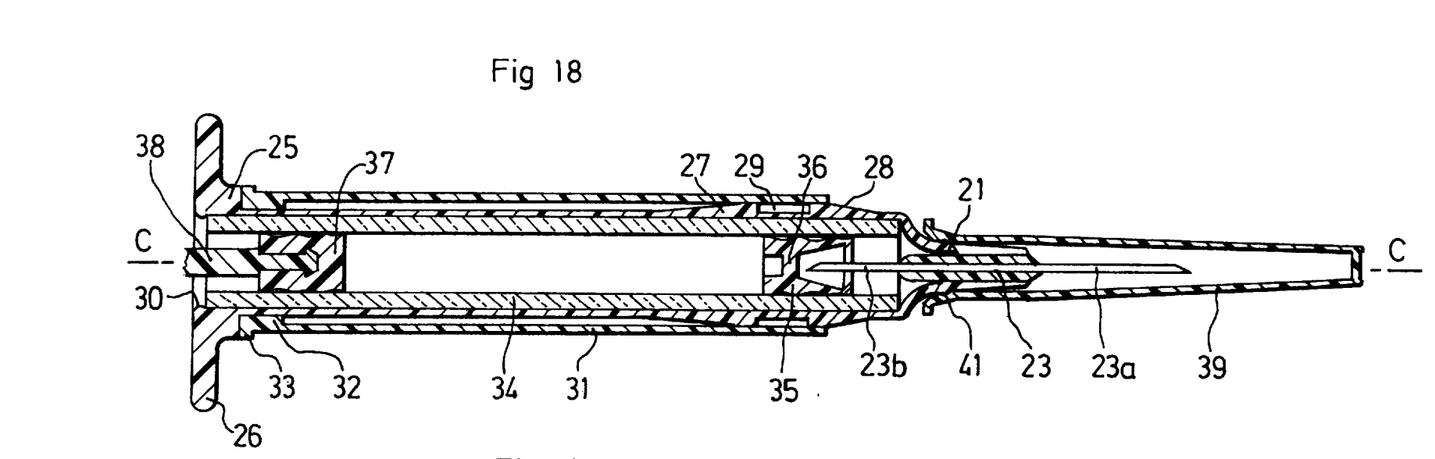
FIG. 18 is a longitudinal section on an axial plane of a fourth embodiment of the injection device according to the invention, shown prior to use.
Figure 19:
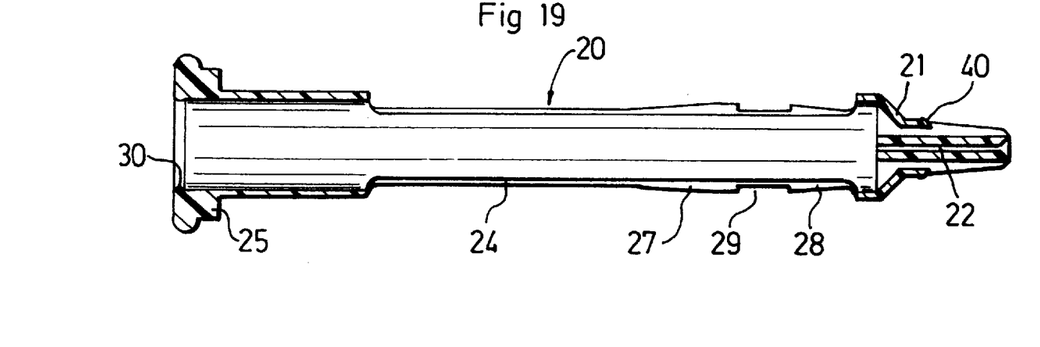
FIG. 19 is a longitudinal section on an axial plane C of the syringe body of this injection device.

The injection device shown in FIG. 18 comprises a tubular syringe body 20, shown in FIG. 19, equipped towards its front end with a nose 21 pierced longitudinally by a bore 22 inside which is introduced an injection needle 23 secured inside the said bore by any known means such as adhesive, so as to provide an active injection portion 23*a* in the extension of the syringe body 1 and a piercing portion 23*b* opening in the interior thereof.

Like the one described with reference to FIGS. 14 to 16 this syringe body 20 comprises two longitudinal slots 24, an external rear shoulder 25 either side of which two finger-hold lugs such as 26 extend and a boss formed by two ramps 27, 28 extending longitudinally either side of an annular groove 29.

In addition, at the rear end of the shoulder 25 this syringe body 20 comprises an internal annular rib 30 intended for the locking in translation of the pre-filled rigid container described below.

For its part, the sheath 31 of this injection device is strictly identical to that described above and thus comprises a rear internal rib 32 arranged to slide along the syringe body 20, and a rear shoulder 33 for resting against the shoulder 25 of the said syringe body.

The rigid container of this injection device comprises a cartridge 34 in the form of a cylindrical tube of dimensions suitable for being housed in the syringe body in which it is locked by the latter's annular rib 30.

At its front end this cartridge 34 is sealed by a plug 35 cut away internally so as to form a membrane 36 suitable for being pierced by the piercing portion 23*b* of the injection needle 23, and at its rear end, by a second plug 37 performing the function of plunger associated with a plunger rod 38.

In addition, these two plugs 35, 37 are arranged so that the membrane 36 of the front plug 35 is at a distance from the rear end of the piercing portion 23*b* of the injection needle 23, as long as the rear plug 37 is not acted on. Because of this, the liquid enclosed in the container 34 is isolated from the injection needle 23 up to the time of the injection.

Finally, this injection device comprises a cap 39 suitable for housing the active portion 23*a* of the injection needle 23, the said cap and the nose 21 of the syringe body comprising paired latching elements suitable for enabling them to be secured in a detachable manner.

In the example, these latching elements comprise an external annular rib 40 provided on the nose 21 and suitable for cooperating with an internal annular groove 41 of the cap 39.

Figures 20, 21, 22:
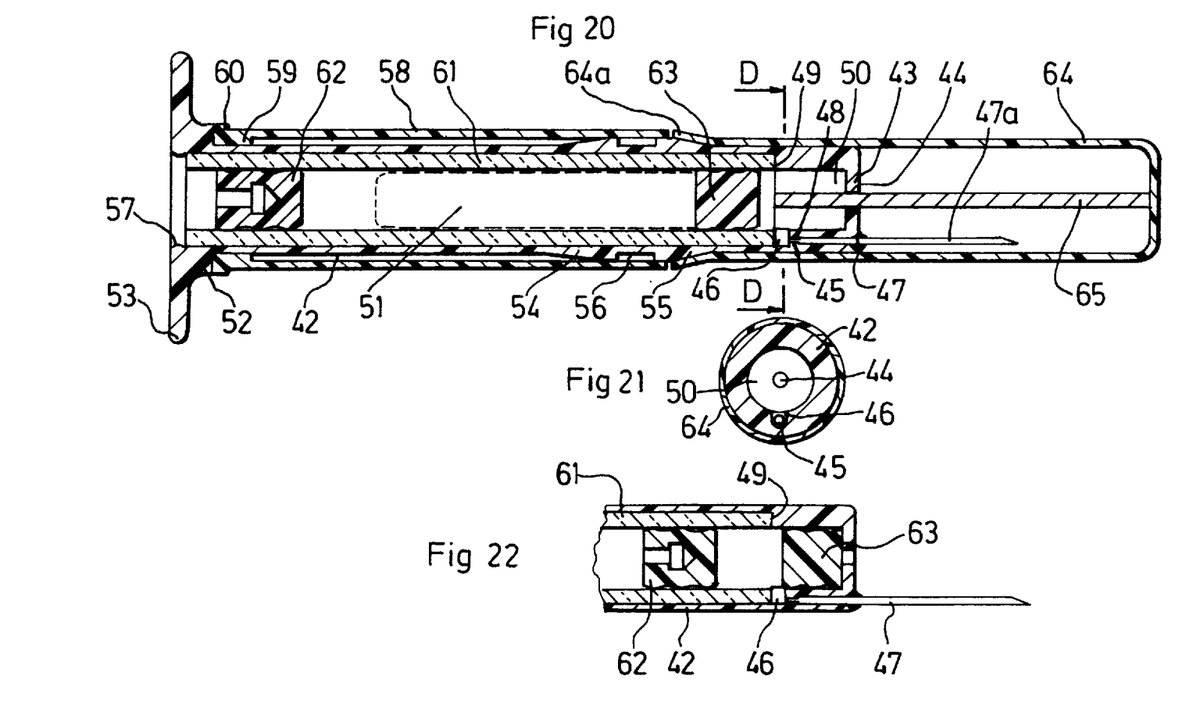
FIG. 20 is a longitudinal section on an axial plane of a fifth embodiment of an injection device according to the invention, shown prior to use.
FIG. 21 is a transverse section thereof on a plane D.
FIG. 22 is a partial longitudinal section on an axial plane of this injection device, shown in the course of injection.

The principles of assembly and use of this injection device are strictly identical to those of the injection devices described above.

or its part the injection device shown in FIGS. 20 to 22 is more specifically designed to be able to inject small doses of liquid.

This injection device comprises a tubular syringe body 42 sealed at its front end by a front wall 43 pierced by an aperture 44.

This syringe body also comprises a longitudinal bore 45 provided in its peripheral wall and extending between the front wall 43 and an internal radial duct 46 opening inside the said syringe body and arranged at a distance from the said front wall.

This longitudinal bore 45 houses an injection needle 47 and comprises an internal intermediate shoulder 48 as a rest for the rear end of the said injection needle and suitable for the latter to have an active injection portion 47*a* in the extension of the front wall 43.

The syringe body also comprises an internal shoulder 49 juxtaposed longitudinally to the radial duct 46, suitable for delimiting, inside the said syringe body, an end chamber 50 incorporating the said radial duct, of smaller cross-section than the standard internal cross-section of this syringe body.

Furthermore, this syringe body 42 comprises two longitudinal slots such as 51, an external rear shoulder 52, either side of which two finger-hold lugs such as 53 extend, and a boss formed of two longitudinal ramps 54, 55 extending either side of an annular groove 56.

Finally, at the rear end of the shoulder 52 this syringe body 42 comprises an internal annular rib 57 for the locking in translation of the pre-filled rigid container.

For its part the sheath 58 of this injection device is strictly identical to those described above and thus comprises a rear internal rib 59 arranged to slide along the syringe body 42, and a rear shoulder 60 as a rest against the shoulder 52 of the said syringe body.

Furthermore, the rigid container comprises a cartridge 61 in the form of a cylindrical tube of dimensions suitable for being housed in the syringe body 42 and extending between the internal shoulder 49 and the latter's rear annular rib 57.

At its rear end this cartridge 61 is sealed by a plug 62 performing the function of plunger, associated with a plunger rod (not shown) and at its front end by a second plug suitable, as shown in FIG. 22, for being housed in the end chamber 50 of the syringe body in a position in which it comes to rest against the front wall 43 and releases the access to the radial duct 46 when the rear plug 62 slides.

Finally, this injection device comprises a cap 64 suitable for covering the front portion of the syringe body 42 and for housing the active portion 47a of the injection needle 47.

This cap 64 of general cylindrical shape has a rear end portion 64a widened in a shape paired with the access ramp 55 of the syringe body 42, suitable for cooperating with it.

Furthermore, an axial rod 65 housed inside this cap 64 is suitable for extending through the aperture 44 of the front wall 42 of the syringe body 42, so as to come into contact with the plug 63 of the cartridge 61. Thus, any displacement of this plug 63 and hence any accidental leakage of the liquid are prevented as long as the cap 64 is in place.

The principles of assembly and use of this injection device are strictly identical to those of the injection devices described above.

Furthermore, because of its design, this injection device has a very low "dead" volume and is particularly suitable for injecting small doses of liquids. Furthermore, because of the position of the injection needle 47 arranged laterally with respect to the syringe body 42, and by means of a correct orientation of the chamfer of the active injection portion 47a of it, this injection device is particularly suitable for permitting an injection (in the abdomen for example) which requires the injection needle to be held in an inclined position with respect to the injection point.

I claim:

1. A process for manufacturing and assembling a pre-filled injection device including an injection needle (116, 15, 23, 47), said process comprising the steps of:

producing a tubular syringe body (101, 121, 1, 20, 42) of a deformable plastic material having a distal end and a proximal end, equipping said proximal end with finger-hold elements (105, 5, 26, 53) and equipping said distal end with an external locking element (104, 123, 7–9, 27–29, 54–56) suitable for deforming radially between a retracted position and a dilated position, producing a tubular sheath (109, 10, 31, 58) of a shape suitable for sliding along said syringe body, providing said tubular sheath with an internal locking element (110, 111, 11, 32, 59) located at a proximal end of said tubular sheath;

locating said proximal end of said sheath adjacent the distal end of said syringe body and slidably inserting said sheath into said syringe body, said sliding being accommodated by radial retraction of said locking element and bringing the said proximal end of said sheath to a position adjacent to said finger-hold elements of said syringe body;

introducing into said syringe body a rigid pre-filled container (114, 13, 34, 61) having an external cross-section which cooperates with the internal cross-section of said syringe body and suitable for bringing said external locking element of said syringe body into a dilated position thereby preventing further radial deformation of said locking element, and equipping said rigid container with means (119, 120; 18, 19; 37, 38; 62) for injecting liquid from said pre-filled container and locking said syringe body and said rigid container against further longitudinal movement with respect to each other.

2. A process as defined in claim 1 further including the step of providing said syringe body with a peripheral wall having at least one longitudinal slot (102, 2, 24, 51) opposite said external locking element suitable for permitting said radial deformation of said locking element.

3. A process as defined in claim 2 further including the steps of equipping said syringe body (20) toward its distal end with a nose (21) pierced longitudinally by a bore (22) of cross-section suitable for accommodating said injection needle (23), introducing said injection needle into said bore of said nose of said syringe body (20), so that said injection needle has an active injection portion (23a) in the extension of said syringe body and a piercing portion (23b) opening into an interior thereof, securing said injection needle (23) in said bore (22) of said nose (21) of said syringe body (20), and introducing into said syringe body a rigid, pre-filled container (34) having a sealing element (35) suitable for being pierced by said piercing portion (23b) of said injection needle (23).

4. A process as defined in claim 2 further including the steps of:

equipping said syringe body (42) with a front end sealed by a front end wall (43) pierced by an aperture (44), and having a longitudinal bore (45) arranged in a peripheral wall thereof, extending between said front wall and a radial internal duct (46) opening into the interior of said syringe body (42), said radial duct (46) being arranged at a distance from said front wall and being juxtaposed longitudinally to a shoulder (49) thus providing inside said syringe body an end chamber (50) incorporating said radial duct (46) thereby providing a smaller cross-section than said internal cross-section of said syringe body, introducing an injection needle (47) into said longitudinal bore (45) so that it has an active injection portion (47a) in the extension of said front wall (43) of said syringe body (42), securing said injection needle 47 in said longitudinal bore (45) of said syringe body (42), and introducing into the interior of said syringe body (42) a rigid pre-filled tube (61) having a cross-section suitable for engaging said shoulder (49) of said syringe body, said rigid tube being sealed adjacent opposite ends thereof by a sliding plug (62, 63), one end of said plug (63) having a shape for fitting within said end chamber (50) when said plug (62) is located to rest against said front wall (43) for disengaging said radial duct (46).

5. A process as defined in claim 1 further including the steps of producing said syringe body to comprise a front end portion (122) in the form of a truncated-cone-shaped portion of decreasing cross-section in the direction of said distal end of said syringe body, and providing said cone-shaped portion with longitudinally extending weakness zones (124) for allowing radial dilation thereof for disabling said locking element (123).

6. A process as defined in claim 1 further including the steps of securing said respective proximal ends of said sheath and of said syringe body in an injection position with holding means suitable for yielding under the effect of longitudinal tensile force applied to said sheath for sliding said sheath over the distal end of said syringe body.

7. a process as defined in claim 1 further including the steps of equipping said syringe body (101; 1) with a distal end in the form of a sleeve (3), inserting into said syringe body a rigid container comprising a pre-filled syringe (114; 13) with an injection needle (116; 15) and having a distal portion of a shape suitable for being accommodated in said sleeve (3) of said syringe body (101; 1), so that said injection needle (116; 15) extends from said distal end of said syringe body.

8. A process as defined in claim 1 including the step of providing a front end of said syringe body (101, 121, 1, 20, 42) with a closure cap.

* * * * *